United States Patent
Pettigrew et al.

(10) Patent No.: US 7,273,961 B2
(45) Date of Patent: Sep. 25, 2007

(54) QUENCH PROCESS

(75) Inventors: Malcolm G. Pettigrew, Houston, TX (US); Wadie Malaty, Houston, TX (US); Ram Mohan Lai Mallik, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 632 days.

(21) Appl. No.: 10/762,495

(22) Filed: Jan. 22, 2004

(65) Prior Publication Data

US 2004/0152939 A1 Aug. 5, 2004

Related U.S. Application Data

(60) Provisional application No. 60/442,346, filed on Jan. 24, 2003.

(51) Int. Cl.
| | |
|---|---|
| C07C 7/00 | (2006.01) |
| C07C 1/00 | (2006.01) |
| C07C 1/20 | (2006.01) |
| C07C 1/207 | (2006.01) |

(52) U.S. Cl. ............ 585/809; 585/603; 585/606; 585/609; 585/639; 585/910

(58) Field of Classification Search ......... 62/121; 585/603, 609, 639, 809, 910, 606
See application file for complete search history.

(56) References Cited

U.S. PATENT DOCUMENTS

| | | | |
|---|---|---|---|
| 3,674,890 A * | 7/1972 | Oleszko et al. ............ 585/535 |
| 6,121,504 A | 9/2000 | Kuechler et al. |
| 6,403,854 B1 * | 6/2002 | Miller et al. ............. 585/638 |

OTHER PUBLICATIONS

Perry's Chemical Engineers' Handbook, 7th ed., p. 7-20.*

* cited by examiner

*Primary Examiner*—Glenn Caldarola
*Assistant Examiner*—Randy Boyer (57) ABSTRACT

The present invention is a process for quenching a reactor effluent stream. The reactor effluent stream comprises water, olefin product, and methanol and is further entrained with catalyst fines. The process removes water, catalyst fines, and methanol. Particularly, methanol removal from the reactor effluent stream is improved.

16 Claims, 1 Drawing Sheet

Fig. 1

QUENCH PROCESS

CROSS REFERENCE TO RELATED APPLICATIONS

The present application claims the benefit of U.S. Provisional Application No. 60/442,346, filed Jan. 24, 2003, said application is incorporated herein by reference.

FIELD OF THE INVENTION

The present invention relates to a process for quenching an effluent stream in a process for converting methanol to an olefin product.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in many processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenates, especially alcohols, are convertible into light olefin(s). The preferred oxygenate for light olefin production is methanol. The process of converting methanol-to-olefins is called the methanol-to-olefin(s) process. There are numerous technologies available for producing oxygenates, and particularly methanol, including fermentation or reaction of synthesis gas derived from natural gas, petroleum liquids, carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Syngas production processes are well known, and include conventional steam reforming, autothermal reforming or a combination thereof.

Syngas is then processed into methanol. Specifically, the components of syngas (i.e., hydrogen, carbon monoxide and/or carbon dioxide) are catalytically reacted in a methanol reactor in the presence of a heterogeneous catalyst. For example, in one process, methanol is produced using a copper/zinc oxide catalyst in a water-cooled tubular methanol reactor.

The methanol-to-olefins reaction is highly exothermic. Moreover, this reaction has a large amount of water. Water comprises as much as one half of the total weight of the effluent stream to isolate the olefins the effluent stream. Consequently, the water must be removed by condensation in a quench device to isolate the olefin product. The quench device cools the effluent stream to the condensation temperature of water. Quenching the product recovers large quantity of water at the temperature near the boiling point of the quench medium. It is desirable to recover heat in higher temperature streams before quenching.

U.S. Pat. No. 6,121,504 describes a quench apparatus for an oxygenate to olefins process as well as a process for using the quench apparatus. The process removes water from the effluent stream as well as some oxygenate feedstock such as methanol.

U.S. Pat. No. 6,403,854 describes a two stage solids wash and quench for use with the oxygenate conversion process. This reference shows that catalyst fines are removed through a first quench stage. Water and methanol is removed in a second quench stage.

It would be desirable to have a quench tower that effectively disposes catalyst fines, removes water and removes oxygenates in an effective and efficient way. The present invention satisfies these and other needs.

SUMMARY OF THE INVENTION

The present invention comprises a staged quench process. Preferably, one embodiment of the present invention comprises a two stage, more preferably a three stage quench. The quench process removes water, catalyst fines and methanol that is present in the reactor effluent stream of an oxygenate to olefin reactor.

In one embodiment, the process comprises the following several steps. The reactor effluent stream is quenched in a first quench stage with a first quench medium. The first quench medium can be an aqueous solution in one embodiment. The quenching in the first quench stage forms a first liquid fraction and a first effluent stream. The first liquid fraction, typically, has no more than 20 wt. % water based upon the weight of water in the reactor effluent stream and also has a majority of catalyst fines from the reactor effluent stream.

Then, the first effluent stream is quenched in a second quench stage with the first quench medium. The quenching in the second quench stage produces a second liquid fraction and a second effluent stream. The quenching in the second quench stage also removes a majority of water from the reactor effluent stream.

The second effluent stream is then quenched in a third quench stage with a second quench medium comprising substantially oxygenate free quench medium. The quenching in the third quench stage removes a majority of the methanol from the second effluent stream.

In another embodiment, the process comprises providing a quench fitting and a first settling vessel. The first settling vessel has a first passage at its top end, a first outlet at its bottom end, and a second outlet between the top end and bottom end. The process further comprises withdrawing the first effluent stream through the first passage. An additional step of separating occurs in the first settling vessel. Particularly, a first portion of catalyst fines are separated from a partially clarified first liquid fraction comprising a second portion of the catalyst fines. The first concentrated fines stream comprising the first portion of catalyst fines is withdrawn from the first outlet. The partially clarified liquid stream comprising the second portion of the catalyst fines is withdrawn from the second outlet.

In yet another embodiment, the partially clarified liquid fraction is directed to a second settling vessel. The second settling vessel settles the partially clarified liquid stream in three portions. The first portion is a second concentrated fines stream. The second concentrated fines stream is withdrawn from the second settling vessel and comprises substantially all of the second portion of catalyst fines from the second settling vessel. Optionally, the second concentrated fines stream is combined with the first concentrated fines stream. The first concentrated fines stream and/or the second concentrated fines stream have from about 3 wt. % to about 90 wt. % catalyst fines based upon the total weight of the second concentrated fines stream.

The second portion in the second settling vessel is a clarified aqueous stream. The second portion is withdrawn from the second settling vessel. The third portion is a non-aqueous portion of the partially clarified liquid stream. It is also withdrawn from the second settling vessel.

In yet another embodiment, the clarified aqueous stream comprises water and methanol. Furthermore, the clarified aqueous stream is separated into a hydrocarbon fraction comprising methanol and a water fraction. In one embodiment, there is from about 25 wt. % to about 90 wt. % methanol in the hydrocarbon fraction. Optionally, the hydrocarbon fraction is recycled back to the reactor as feed.

In another embodiment, the second quench stage has a first quench inlet and a second quench inlet. The second quench inlet is located above the first quench inlet. The process further comprises a step of introducing quench medium into the first quench inlet at a first temperature and the second quench inlet at a second temperature. The second temperature is at least about 5° F. (2.7° C.), preferably 10° F. (5.6° C.), more preferably at least 20° F. (11° C.), lower than the first temperature.

In one embodiment there is a process for removing methanol from a reactor effluent stream of an oxygenate to olefin reactor. The process of this embodiment comprises quenching the reactor effluent stream with a first quench medium to remove at least 75 wt. % water based upon the total weight of water in the reactor effluent stream. The quenching with a first quench medium produces a quenched effluent stream. Next, the quenched effluent stream is quenched with a second quench medium. The quenching with the second quench medium removes a majority of methanol in the already quenched effluent stream. In one embodiment, the process steps described above are done at a pressure of below about 40 psig (276 kPag), preferably below about 25 psig (172 kPag), more preferably below about 10 psig (69 kPag).

Another embodiment comprises a process for quenching an effluent stream. The effluent stream comprises water, olefin product, and methanol, and is entrained with catalyst fines. The process comprises the steps of: (a) removing at least 80 wt. % of the water from the effluent stream; (b) separating at least 95 wt. % of the catalyst fines from the effluent stream; and (c) removing at least 97 wt. % of the methanol from the effluent stream. Steps (a) (b) and (c) above are done in a single quench tower apparatus. Preferably, step (c) of the process above removes at least 98 wt. %, preferably at least 99 wt. %; more preferably at least 99.75 wt. % of methanol.

In yet another embodiment, there is a process for quenching a reactor effluent stream. The reactor effluent stream comprises water, olefin product, and methanol. The reactor effluent stream is entrained with catalyst fines. At least 80 wt. % of the water in the reactor effluent stream is removed from the reactor effluent stream. At least 95 wt. % of catalyst in the reactor effluent stream is removed from the reactor effluent stream. At least 97 wt. %, preferably at least 98 wt. %, more preferably at least 99 wt. %, most preferably at least 99.75 wt. % of the methanol in the reactor effluent stream is removed from the reactor effluent stream. The process occurs at a pressure of less than 40 psig (276 kPag).

In still another embodiment, quench process of a reactor effluent stream withdrawn from a reactor in a process for converting methanol into olefin product. The reactor effluent stream comprises olefin product, water, and methanol and is entrained with catalyst fines. The process comprises the steps of: (a) contacting the reactor effluent stream with a first quench medium in a first quench stage; (b) withdrawing a first liquid stream from the reactor effluent stream to form a first effluent stream, the first liquid stream comprising catalyst fines and water; (c) contacting the first effluent stream with the first quench medium in a second quench stage; and (d) cooling a portion of the first quench medium to form a cooled first quench medium and contacting the first effluent stream with the first cooled quench medium in the second quench stage; (e) withdrawing a second liquid stream in the second quench stage to form a second effluent stream; (f) contacting, in a third quench stage, the second effluent stream with a second quench medium comprising substantially oxygenate free quench medium; and (g) withdrawing a third liquid stream in the third quench stage to form a third effluent stream. The third liquid stream comprises water and methanol.

According to one embodiment, steps (b) through (g) are done in a single multi-staged quench tower. In another embodiment, the first quench medium is at least 5° F. (2.7° C.) lower than the second quench medium. In still another embodiment, steps (a) through (g) are done at a pressure of no greater than 40 psig (276 kPag). The first liquid stream comprises no less than 50 wt. % catalyst fines based upon the total weight of catalyst fines in the reactor effluent stream.

According to yet another embodiment, there is a process for removing methanol from a reactor effluent stream using a quench device, the process comprising the steps of: (a) passing a reactor effluent stream through two quench stages using the same quench medium to form a second effluent stream; and (b) introducing the second effluent stream to at least one or more quench stages to produce a third effluent stream that has no more than 95 wt. %.

DETAILED DESCRIPTION OF THE INVENTION

Introduction

The present invention is directed to a process for quenching a reactor effluent stream. The reactor effluent stream comprises water, olefin product, and methanol, and is further entrained with catalyst fines. The process removes water, catalyst fines, and methanol in preferably at least three stages. When three stages are utilized in the process of the invention, the third stage removes methanol from the reactor effluent stream. The process of the present invention, including one or more embodiments is described in detail below.

The Oxygenate to Olefin Process

The molecular sieve catalyst compositions are particularly useful in processes for conversion of a feedstock contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols that are useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstock discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbon atoms, and most preferably ethylene an/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexenene-1 and isomers thereof. Other olefin monomer(s) include unsaturated monomers, diolefins having 4 to 18 carbon atoms, conjugated or non-conjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, and most preferably methanol, to the preferred olefin(s) ethylene and/or propylene.

The are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as methanol-to-olefins (MTO). In a MTO process, typically an oxygenated feedstock and most preferably a methanol containing feedstock, is converted in the presence of a methanol to olefins catalyst or catalyst composition. In one embodiment, the catalyst or catalyst composition is molecular sieve catalyst composition into one or more olefins(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent.

As noted, oxygenate to olefin processes use molecular sieve catalysts or catalyst compositions. The molecular sieve catalysts or catalyst compositions have molecular sieve and binder and/or matrix material. The molecular sieve catalysts are prepared according to techniques that are known to a person of ordinary skill in the art.

Molecular sieve include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, AFO, AEL, EUO, HEU, FER, MEL, MFI, MTW, MTT, TON, EMT, FAU, ANA, BEA, CFI, CLO, DON, GIS, LTL, MER, MOR, MWW and SOD and substituted forms thereof; and the large pore molecular sieves. Preferably the molecular sieve is a zeolitic or zeolitic-type molecular sieve. Alternatively, the preferred molecular sieve is an aluminophosphate (ALPO) molecular sieves and silicoaluminophosphate (SAPO) molecular sieves and substituted, preferably metal substituted, ALPO and SAPO molecular sieves including the molecular sieves that are intergrowth materials having two or more distinct phases of crystalline structures within one molecular sieve composition.

Binder materials that are useful alone or in combination include various types of hydrated alumina, silicas, and/or other inorganic oxide sol. In one embodiment, the binders are alumina sols including include Nalco 8676 available from Nalco Chemical Co., Naperville, Ill., and Nyacol available from The PQ Corporation, Valley Forge, Pa.

Matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, and most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butene, pentene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system, and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite, zeolite-type molecular sieve catalyst, silicaluminophosphate catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 1 weight percent to about 10 weight percent based on the total weight of the feedstock including any diluent contained therein. The liquid and vapor feedstocks are preferably of similar composition, or contain varying proportions of the same or different feedstock with the same or different diluent.

The feedstock entering the reactor system is preferably converted, partially or fully, in the first reactor zone into a effluent stream that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the effluent stream containing one or more olefin(s) within the disengaging zone. Cyclones are preferred, however, gravity effects within the disengaging vessel will also separate the catalyst compositions from the effluent stream. Other methods for separating the catalyst compositions from the effluent stream include the use of plates, caps, elbows, and the like. Cyclones are particle size separators and retain catalyst above a threshold size. Catalyst below a threshold size pass through the cyclones in the effluent stream. As defined above, catalyst particles are retained by the cyclones in the reactor. Catalyst fines pass through the cyclones into the effluent stream.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from about 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C., and most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically, the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock-containing methanol and dimethyl ether is in the range of from about 20 hr$^{-1}$ to about 300 hr$^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 hr$^{-1}$ and a Temperature Corrected Normalized Methane Selectivity (TCNMS) of less than 0.016, preferably less than or equal to 0.01. See, for example, U.S. Pat. No. 5,952,538 that is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kpaa) to about 150 psia (1034 kpaa), and most preferably from about 30 psia (207 kPaa) to about 60 psia (414 kpaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the effluent stream (PCT WO 00/49106 published Aug. 24, 2000), which are all herein fully incorporated by reference. In another embodiment, a regenerated molecular sieve catalyst composition contacted with an alcohol, preferably ethanol, 1-propanol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, the optimum level of coke on the molecular sieve catalyst composition in the reaction zone is maintained by controlling the flow of the regenerated molecular sieve catalyst composition or cooled regenerated molecular sieve catalyst composition from the regeneration system to the reactor system. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336-337), which is herein incorporated by reference. This is referred to as the complete regeneration mode. In another embodiment, the optimum level of coke on the molecular sieve catalyst composition in the reaction zone is maintained by controlling the flow rate of the oxygen-containing gas flow to the regenerator. This is referred to as the partial regeneration mode.

Coke levels, or the level of carbonaceous deposits, on the molecular sieve catalyst composition are measured by withdrawing from the conversion process the molecular sieve catalyst composition at a point in the process and determining its carbon content.

In one preferred embodiment, the molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated catalyst and catalyst that has ranging levels of carbonaceous deposits. The measured level of carbonaceous deposits thus represents an average of the levels an individual catalyst particle.

Effluent Stream Quench and Catalyst Fines Recovery

Figure 1:
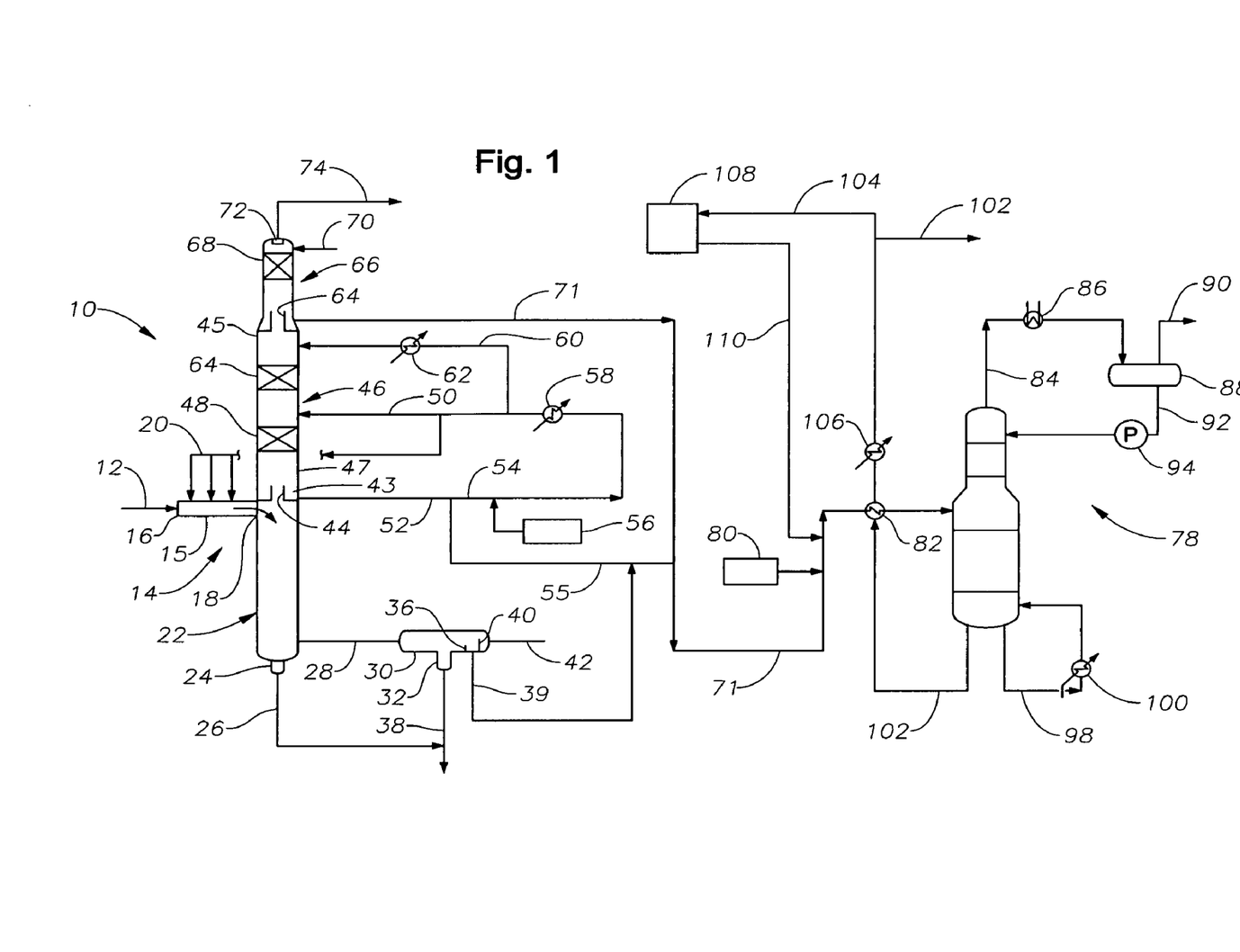
FIG. 1 illustrates a process scheme according to one embodiment of the present invention.

FIG. 1 illustrates one embodiment of the present invention. The oxygenate to olefin reaction occurs in a reactor and produces an effluent stream. The effluent stream is defined as the output of the reactor effluent that remains in the gaseous state from the reactor to the product recovery section. The effluent stream is quenched according to one embodiment of the present invention. The composition of the effluent stream from the point it leaves the reactor to the first step of quenching is defined as the reactor effluent stream. The composition of the reactor effluent stream is determined at the point it leaves the reactor, unless specified otherwise. The reactor effluent stream comprises ethylene and propylene, $C_{4+}$ olefins, methane, C2+ parafins, water, unreacted oxygenate feedstock, and oxygenate hydrocarbons The reactor effluent stream travels along line 12 and enters the pre-quench or first quench stage 14.

According to one embodiment, the weight of ethylene expressed as a percentage of the total weight of the reactor effluent stream is preferably from about 14 wt. % to about 18 wt. %, more preferably from about 15 wt. % to about 17 wt. %; and most preferably about 16 wt. % According to one embodiment, the weight of propylene expressed as a percentage of the total weight of the reactor effluent stream is preferably from about 14 wt. % to about 18 wt. %, more preferably from about 15 wt. % to about 17 wt. %; and most preferably about 16 wt. %

According to one embodiment, the weight of water expressed as a percentage of the total weight of the reactor effluent stream is from about 55 wt. % to about 65 wt. %; preferably about 59 wt. % According to one embodiment, the weight of C4+ olefins expressed as a percentage of the total weight of the reactor effluent stream is from about 4 wt. % to about 7 wt. %; preferably 5.6 wt. %

According to another embodiment, the weight of methanol expressed as a percentage of the total weight of the reactor effluent stream is from about 0.5 wt. % to about 1.5 wt. %; preferably about 1 wt. % According to one embodiment, the weight of oxygenates other than methanol expressed as a percentage of the total weight of the reactor effluent stream is from about 0.5 wt. % to about 1.5 wt. %; preferably about 1 wt. % According to one embodiment, the weight of alkanes expressed as a percentage of the total weight of the reactor effluent stream is from about 5 wt. % to about 50 wt. %; preferably from about 25 wt. % to about 35 wt. %; and most preferably about 29 wt. %

The first quench stage 14 of one embodiment has a quench fitting 15 and a settling vessel 22. The quench fitting 15 is shown here in FIG. 1 by example is generally horizontal. The quench fitting 15 has an inlet 16 and an outlet 18. The outlet 18 is in fluid communication with the first settling vessel 22 by means of a conduit 19. According to one embodiment, the temperature of quench medium entering the inlet 16 of the quench fitting 15 is from about 70° F. (21° C.) to about 180° F. (82.2° C.); preferably from about 80° F. (27° C.) to about 130° F. (54° C.); and most preferably from about 80° F. (27° C.) to about 120° F. (49° C.).

According to an embodiment, the temperature of the reactor effluent stream entering the quench has been cooled by one more heat exchangers, preferably two to six heat exchangers, more preferably two to four heat exchangers, most preferably four heat exchangers. The temperature of the reactor effluent stream entering the quench tower is preferably from about 200° F. (93° C.) to about 400° F. (204° C.); more preferably from about 200° F. (93° C.) to about 350° F. (177° C.); most preferably from about 200° F. (93° C.) to about 300° F. (149° C.). In on embodiment, the reactor effluent stream has a condensation temperature defined as the temperature that one or more components of the reactor effluent stream begin to condense at a given pressure. According to one embodiment, the reactor effluent stream enters the first quench stage at a temperature ranging from about 1° F. (−17° C.) to about 100° F. (38° C.) preferably from about 1° F. (−17° C.) to about 50° F. (10° C.); more preferably from about 1° F. (−17° C.) to about 25° F. (−3.8° C.) above the condensation temperature of the reactor effluent stream.

In another embodiment, the volume of quench medium used in the first quench stage 14 expressed as a weight percentage of the total amount of water in the reactor effluent stream entering the first quench stage 14 ranges from about 10 wt. % to about 30 wt. %; preferably from about 20 wt. % to about 30 wt. %; most preferably about 25 wt. %.

The reactor effluent stream is partially condensed in the first quench stage 14 (or pre-quench) to form a first liquid fraction and a first quenched effluent stream. The first quenched effluent stream or first effluent stream is defined as the effluent stream in a gaseous state as it leaves the first quench stage 14 and passes into the second quench stage 46. The composition of the first quench stage 14 is determined at the time the first effluent stream leaves the first quench stage 14. According to one embodiment, illustrated in FIG. 1, the composition of the first effluent stream is determined as the first effluent stream passes through passage 44. The first liquid fraction is defined as the liquid that condenses in the first quench stage 14. In one embodiment, illustrated in FIG. 1, the first liquid fraction is defined as the liquid composition in the first settling vessel 22. Preferably, the first liquid fraction comprises no less than 90 wt. % catalyst fines based upon the total weight of catalyst fines in the reactor effluent stream. The first liquid fraction comprises no greater than about 20 wt. % water based upon the total weight of water in the reactor effluent stream.

In one embodiment, the reactor effluent stream is partially condensed. Partial condensation of a particular effluent stream, as used in this application, means that less than 90 wt. % of the water in the particular effluent stream is condensed. This step of partially condensing the effluent stream results in a greater concentration of solids in the first liquid fraction than would have been if greater than 90 wt. % of the water in the reactor effluent stream is condensed into the first liquid fraction. In another embodiment, the reactor effluent is cooled but not condensed in the first quench stage 14. Cooling without condensing occurs when the amount of water in the first liquid fraction is less than the amount of quench medium added in the first quench stage 14. According to one embodiment, the first liquid fraction comprises no more than about 15 wt. %; preferably from about 3 wt. % to about 10 wt. %, more preferably about 10 wt. % based upon the total weight of the water in the reactor effluent stream.

In one embodiment, the contacting of first quench medium with the reactor effluent stream occurs as the reactor effluent stream travels through the generally tubular quench fitting 15 defining a wall of the quench fitting 15 through a plurality of nozzles. The quench medium is sprayed inward from the walls of the quench fitting 15. A sufficient quantity of liquid quench medium is sprayed into the quench fitting 15 to cause contact between the liquid droplets and the catalyst fines that are entrained in the reactor effluent stream.

The catalyst fines are washed from the reactor effluent stream into the first liquid fraction. The mixture of gas, liquid and solid leaves the quench fitting through the outlet 18 into the first settling vessel 22. The first settling vessel 22 is configured to (1) separate the first liquid fraction and catalyst fines from the first effluent stream and (2) cause settling, or at least partial settling, of the catalyst fines that are entrained in the first liquid fraction. The first effluent stream passes through passage 44. The catalyst fines in the first liquid fraction settle into the lower part of the first settling vessel 22 into a boot 24 to improve the settling of the catalyst fines.

The catalyst fines that are concentrated in the boot 24 are withdrawn along line 26. The stream in line 26 is a concentrated fines stream. A condensed fines stream is a stream that has a concentration of catalyst fines that is greater than the concentration of catalyst fines in the first liquid fraction. According to one embodiment, the concentration of catalyst fines in the first liquid fraction is determined as the first liquid fraction enters the first settling vessel 22. The concentrated fines stream is conveyed to a catalyst fines de-watering system (not shown) that further concentrates the catalyst fines by removing more water from the catalyst fines.

According to an embodiment, a second outlet on the first settling vessel 22 of the pre-quench 14 removes quench medium along line 28 to a second settling vessel 30. In this second settling vessel 30, particulate matter in water settles to the bottom of the second settling vessel and into the boot 32. The catalyst fines are concentrated in the boot 32 and removed along line 38. The stream in line 38 is a concentrated fines stream and is combined with the concentrated fines stream in line 26. The combined stream is conveyed to the catalyst fines de-watering system (not shown). The weight of catalyst fines expressed as a percentage of the weight of the total stream in lines 38 and 26 is from about 0.25 wt. % to about 10 wt. %; preferably from about 1 wt. % to about 10 wt. %, more preferably about 3 wt. %

The second settling vessel 30 is baffled with a first baffle 36, according to one embodiment. The first baffle permits separation of clarified aqueous liquid from the catalyst fines. The clarified aqueous liquid is removed from the second settling vessel 30 along line 39 that is further processed to remove methanol via distillation as described below.

A second baffle 40 of the second settling vessel 30 separates the aqueous phase from a hydrocarbon phase. The hydrocarbon phase comprises high boiling point hydrocarbon products and byproducts. The hydrocarbon phase is removed from the second settling vessel 30 along lines 42. The hydrocarbon phase can be efficiently disposed in a conventional olefins recovery system by transporting it and combining it with the debutanizer bottoms stream.

The second quench stage 46 of the quench 10 removes substantially all of the water in the first effluent stream and separates a second effluent stream from the second liquid stream. The second effluent stream is defined as the gaseous portion of the first effluent stream that leaves the second quench stage 45 and enters a third quench stage 66. The composition of the second effluent stream is determined as it leaves the top end 45 of the second quench stage 46. The second liquid fraction is the liquid portion that is condensed in the second quench stage 46. The phrase "substantially all" means at least 75%. Preferably, it is advantageous to remove as much water as is efficiently possible from the first effluent stream in the second quench stage 46. Nonetheless, some water remains in the second effluent stream when it leaves the second quench stage 46. Particularly, water that is saturated in the second effluent stream under the particular temperature and pressure conditions of the second quench stage 46 remain in the second effluent stream.

Typically, the second effluent stream comprises no more than 15 wt. % water based upon the total weight of water in the reactor effluent stream. Preferably, the second effluent stream comprises no more than 10 wt. % water based upon the total weight of water in the reactor effluent stream.

The second quench stage 46 has a top end 45 and a bottom end 47. According to one embodiment, the temperature of the first effluent stream as it leaves the first quench stage 14 and enters the second quench stage 46 at the bottom end 47 of the second quench stage 46 adjacent passage 44 is from about 160° F. (71° C.) to about 275° F. (133° C.), preferably from about 210° F. (99° C. to about 230° F. (110° C.), more preferably about 220° F. (104° C.). The temperature of the second effluent stream at the top end of the second quench stage 66 ranges from about 80° F. (27° C.) to about 130° F. (54° C.); preferably from about 90° F. (32° C.) to about 125° F. (52° C.); and most preferably about 120° F. (49° C.).

As noted previously, the bottom end 47 of the second quench stage is fitted with passage 44. The walls of the passage define on its opposite side of the passage a collection vessel 43 into which second liquid fraction collects. As the first effluent stream travels upward, it passes through two quench zones. A first quench zone 48 is quenched by a quench medium fed along line 50. A second quench zone 64 is quench by a quench medium that is fed along line 60. The quench medium, equilibrium condensed effluent water, oxygenates and hydrocarbons travel downward through the column packing in the first zone 64 and second zone 48 and contacts the upward moving first effluent stream. As the contact occurs, part of the first effluent stream continues to condense and collect in the in the collection vessel 43 at the bottom 47 of the second quench stage 46 as the second liquid fraction.

The second liquid fraction is removed from the collection vessel in the bottom of the second quench stage 46 via line 52. A portion of the second liquid fraction in line 52 is removed to a recovery tower 78 along line 55. According to one embodiment, line 39 from the second settling vessel 30 is combined with line 55 before being sent to the recovery tower 78. Tower 78 removes methanol, other oxygenates and light hydrocarbons via distillation.

A portion of the second liquid fraction in line 52 is conveyed along the quench recycle line 54. Line 54 is cooled by a heat exchanger 58. Optionally, a corrosion inhibitor injection package 56 injects corrosion inhibitor into line 54. The corrosion inhibitor package comprises a dosing vessel and a dosing pump.

The quench recycle line 54 is cooled in heat exchanger 58 to make the first quench medium. A first quench portion of the first quench medium is sent to the pre-quench 14 along line 20. The temperature of the first quench medium entering the pre-quench along line 20 ranges from about 100° F. (38° C.) to about 150° F. (66° C.); more preferably from about 110° F. (43° C.) to about 130° F. (54° C.); and most preferably about 120° F. (49° C.).

A second quench portion of the first quench medium supplies a first quench zone 48 in the second quench stage 46 along line 50 and feeds the first quench zone 48 of the second quench stage 46. The temperature of the first quench medium entering the first quench zone 48 of the second quench stage 46 ranges from about 100° F. (38° C.) to about 150° F. (66° C.); preferably from about 118° F. (48° C.) to about 130° F. (54° C.); and most preferably from about 120° F. (49° C.).

A third quench portion travels along line 60 and is further cooled by heat exchanger 62. The third quench portion cools the second quench zone 64 of the second quench stage 46. The temperature of the quench medium prior to entering the second quench zone 64 of the second quench stage 46 is preferably from about 80° F. (27° C.) to about 130° F. (54° C.); more preferably from about 90° F. (32° C.) to about 120° F. (49° C.); and most preferably about 100° F. (38° C.).

In one embodiment, substantially all of the water is quenched by the second quench stage 46 to form the second effluent stream, which passes through passage 64 into the third quench stage 66. The second effluent stream is quenched by a second quench medium in the third quench stage 66. The third quench stage 66 has a top end and a bottom end. The second effluent stream travels from the bottom end to the top end. As it moves upward, the second effluent stream passes through a quench packing 68 to cause intimate contact between the second effluent stream and the second quench medium. The gaseous portion of the second effluent stream that exits the third quench stage is defined as the third effluent stream or olefin product stream. The temperature of the third effluent stream at the top end of the third quench stage 66 ranges from about 50° F. (10° C.) to about 120° F. (49° C.); preferably from about 60° F. (16° C.) to about 110° F. (43° C.); and most preferably about 105° F. (41° C.). Preferably, according to an embodiment, the third effluent stream comprises no more than 3 wt. % methanol based upon the total weight of methanol in the reactor effluent stream.

The second quench medium that quenches the third quench stage of one embodiment is preferably fresh water. By fresh water, it is meant water that has less than 10 wppm salt and less than 100 wppm hydrocarbon, including oxygenated hydrocarbons. In another embodiment, the second quench medium is substantially oxygenate free quench medium that has less than 75 wppm oxygenate hydrocarbons. In yet another embodiment, the water has less than 50 wppm alcohol preferably less than 10 wppm more preferably less than 5 wppm most preferably less than 1 wppm. In yet another embodiment, the water has less than 50 wppm methanol preferably less than 10 wppm more preferably less than 5 wppm most preferably less than 1 wppm.

In another embodiment, the second quench medium that quenches the second effluent stream is substantially oxygenate free quench medium from the bottoms stream 102 of the methanol recovery tower 78. In one embodiment, the substantially oxygenate free quench medium or fresh water extracts methanol from the effluent stream. The substantially oxygenate free quench medium is supplied along line 70 and enters the third quench stage 66 at the top end of third quench stage. The substantially oxygenate free quench medium (or fresh water) and quenched effluent from the second effluent stream defines a third liquid fraction. The third liquid fraction is removed from the bottom end of the third quench stage 66 along line 71. In one embodiment, line 71 is connected to lines 39 and 55. At least one or all of lines 71, 39, and 55 supply water to the methanol recovery tower 78. The quench bottoms from the third quench stage along line 71 as well as other related streams (lines 39 and 55) are sent to a methanol recovery tower 78 or methanol stripper.

A mist eliminator 72 covers the overhead exit of the top of the third quench stage 66 to capture any portion of the third liquid fraction or quench medium that is entrained in the vapor stream. The third effluent stream is carried along line 74 to product recovery.

Line 71 contains unreacted methanol product that is carried in the reactor effluent stream in addition to quench medium and water from the reactor effluent stream. Line 71 can have, in some instances, at least some catalyst fines. In one embodiment, the stream passes through a filter (not shown) to remove all catalyst fines or other particulate. The feed along line 71 is first heated by a portion of the bottoms of the methanol recovery tower (line 104) in heat exchanger 82.

The methanol recovery tower 78 separates methanol and other hydrocarbons in line 71 from the water in the same stream. Line 71 is fed into the methanol recovery tower and is separated into an overhead stream (i.e., at the top of the tower) and a bottoms stream (i.e., at the bottom of the tower). The compounds with high relative volatility (i.e., boil at lower temperatures) are withdrawn from the overhead stream. The compounds with low relative volatility (i.e., boil at higher temperatures) are withdrawn from the bottoms stream. According to one embodiment, methanol is recovered in the overhead stream. Additionally, any components in the stream of line 71 that have a higher relative volatility than methanol are boiled in the overhead stream.

According to an embodiment, there is still a considerable amount of water in the overhead stream. Particularly, there is from about 25 wt. % to about 75 wt. % methanol. According to another embodiment, there is no more than 300 wppm methanol in the bottoms streams, preferably no more than 250 wppm methanol.

Methanol vapors are withdrawn from the overhead stream of the methanol recovery tower 78 along line 84 and cooled in an overhead condenser 86. Vaporizing methanol feed, in one embodiment condenses the overhead stream from line 84, or at least partially condenses the overhead stream. The overhead stream is then sent back to a knock out drum 88. The condensed overhead stream is withdrawn along line 92 and is pumped into the top of the methanol recovery tower 78. According to one embodiment, the methanol vapor is withdrawn along line 90 and is recovered and recycled back to the methanol feed vaporization drum (not shown) where it is vaporized and used as feed in the oxygenate to olefin reactor.

The bottoms 97 of the methanol recovery tower 78 comprises a substantially methanol free liquid water stream. Methanol content in the water is preferably below 100 wppm. A portion of the bottoms of the methanol recovery tower 78 is withdrawn along line 98, reboiled in heat exchanger 100 and recycled back to the bottoms of the methanol recovery tower 78. The water that is reboiled is called reboiler water. A portion of the methanol recovery tower bottoms is withdrawn along 102 and is used to heat the methanol feed in heat exchanger 82. Another portion of line 102 is further processed and eventually disposed as wastewater.

Optionally, a portion of the wastewater is withdrawn along line 104 to an off-spec storage vessel 108. An "off-spec storage vessel" is a storage vessel for water that does not meet a predetermined specification for water composition. Typically, the specification requires methanol levels below an acceptable level for waste water treatment. The off-spec storage vessel and pump is provided to divert the bottoms stream of the methanol recovery tower 78 in line 102 to the storage vessel in case of any problem with tower operation resulting in higher than acceptable levels of methanol in the water. The water accumulated in the storage tank is redirected along line 110 to the line 71 that feeds the methanol recovery tower for further processing. According to one embodiment, the off-spec water tank can hold an 8-hour normal production of water.

Product Recovery

After the third effluent stream or olefin product stream passes through the quench 10, it is further processed to isolate and purify components in the effluent stream, particularly, ethylene and propylene. There are many well-known recovery systems, techniques and sequences that are useful in separating olefin(s) and purifying olefin(s) from the effluent stream. Recovery systems generally comprise one or more or a combination of a various separation, fractionation and/or distillation towers, columns, splitters, or trains, reaction systems and other associated equipment for example various condensers, heat exchangers, refrigeration systems or chill trains, compressors, knock-out drums or pots, pumps, and the like.

Non-limiting examples of equipment used in a recovery system include one or more of a demethanizer, preferably a high temperature demethanizer, a dethanizer, a depropanizer, a wash tower often referred to as a caustic wash tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249-271 and 894-899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent stream withdrawn from the reactor or converting those products produced as a result of the recovery system utilized.

In one embodiment, the effluent stream withdrawn from the reactor is passed through a recovery system producing one or more hydrocarbon containing stream(s), in particular, a three or more carbon atom ($C_3^+$) hydrocarbon containing stream. In this embodiment, the $C_3^+$ hydrocarbon containing stream is passed through a first fractionation zone producing a crude $C_3$ hydrocarbon and a $C_4^+$ hydrocarbon containing stream, the $C_4^+$ hydrocarbon containing stream is passed through a second fractionation zone producing a crude $C_4$ hydrocarbon and a $C_5^+$ hydrocarbon containing stream. The four or more carbon hydrocarbons include butenes such as butene-1 and butene-2, butadienes, saturated butanes, and isobutanes.

The effluent stream removed from a conversion process, particularly a MTO process, typically has a minor amount of hydrocarbons having 4 or more carbon atoms. The amount of hydrocarbons having 4 or more carbon atoms is typically in an amount less than 30 weight percent, preferably less than 25 weight percent, more preferably less than 20 weight percent, and most preferably less than 15 weight percent, based on the total weight of the effluent stream withdrawn from a MTO process, excluding water. In particular with a conversion process of oxygenates into olefin(s) utilizing a molecular sieve catalyst composition the resulting effluent stream typically comprises a majority of ethylene and/or propylene and a minor amount of four carbon and higher carbon number products and other by-products, excluding water.

Suitable well-known reaction systems as part of the recovery system primarily take lower value products and convert them to higher value products. For example, the $C_4$ hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel.

Non-limiting examples of reaction systems include U.S. Pat. No. 5,955,640 (converting a four carbon product into butene-1), U.S. Pat. No. 4,774,375 (isobutane and butene-2 alkylated to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all herein fully incorporated by reference.

The preferred light olefin(s) produced by any one of the processes described above, preferably conversion processes, are high purity prime olefin(s) products that contains a $C_x$ olefin, wherein x is a number from 2 to 4, in an amount greater than 80 wt. %, preferably greater than 90 wt. %, more preferably greater than 95 wt. %, and most preferably no less than about 99 wt. %, based on the total weight of the olefin.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent stream fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas.

Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein fully incorporated by reference.

In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000 that is herein fully incorporated by reference.)

Polymerization processes include solution, gas phase, slurry phase and a high-pressure process, or a combination thereof. Particularly preferred is a gas phase or a slurry phase polymerization of one or more olefin(s) at least one of which is ethylene or propylene. Polymerization processes include those non-limiting examples described in the following: U.S. Pat. Nos. 4,543,399, 4,588,790, 5,028,670, 5,317,036, 5,352,749, 5,405,922, 5,436,304, 5,453,471, 5,462,999, 5,616,661, 5,627,242, 5,665,818, 5,677,375, 5,668,228, 5,712,352 and 5,763,543 and EP-A-0 794 200, EP-A-0 802 202, EP-A2-0 891 990 and EP-B-0 634 421 describe gas phase polymerization processes; U.S. Pat. Nos. 3,248,179 and 4,613,484, 6,204,344, 6,239,235 and 6,281,300 describe slurry phase polymerization processes; U.S. Pat. Nos. 4,271,060, 5,001,205, 5,236,998 and 5,589,555 describe solution phase polymerization processes; and U.S. Pat. Nos. 3,917,577, 4,175,169, 4,935,397, and 6,127,497 describe high pressure polymerization processes; all of which are herein fully incorporated by reference.

These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. Non-limiting examples of polymerization catalysts are described in U.S. Pat. Nos. 3,258,455, 3,305,538, 3,364,190, 3,645,992, 4,076,698, 4,115,639, 4,077,904 4,482,687, 4,564,605, 4,659,685, 4,721,763, 4,879,359, 4,960,741, 4,302,565, 4,302,566, 4,302,565, 4,302,566, 4,124,532, 4,302,565, 5,763,723, 4,871,705, 5,120,867, 5,324,800, 5,347,025, 5,384,299, 5,391,790, 5,408,017, 5,491,207, 5,455,366, 5,534,473, 5,539,124, 5,554,775, 5,621,126, 5,684,098, 5,693,730, 5,698,634, 5,710,297, 5,714,427, 5,728,641, 5,728,839, 5,753,577, 5,767,209, 5,770,753 and 5,770,664, 5,527,752, 5,747,406, 5,851,945 and 5,852,146, all of which are herein fully incorporated by reference.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a zeolite or zeolite-type molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

Polymerization conditions vary depending on the polymerization process, polymerization catalyst system and the polyolefin produced. Typical conditions of polymerization pressure vary from about 100 psig (690 kPag) to greater than about 1000 psig (3448 kPag), preferably in the range of from about 200 psig (1379 kPag) to about 500 psig (3448 kPag), and more preferably in the range of from about 250 psig (1724 kPag) to about 350 psig (2414 kPag). Typical conditions of polymerization temperature vary from about 0° C. to about 500° C., preferably from about 30° C. to about 350° C., more preferably in the range of from about 60° C. to 250° C., and most preferably in the range of from about 70° C. to about 150° C. In the preferred polymerization process the amount of polymer being produced per hour is greater than 25,000 lbs/hr (11,300 Kg/hr), preferably greater than 35,000 lbs/hr (15,900 Kg/hr), more preferably greater than 50,000 lbs/hr (22,700 Kg/hr) and most preferably greater than 75,000 lbs/hr (29,000 Kg/hr).

The polymers produced by the polymerization processes described above include linear low density polyethylene, elastomers, plastomers, high density polyethylene, low density polyethylene, polypropylene and polypropylene copolymers. The propylene-based polymers produced by the polymerization processes include atactic polypropylene, isotactic polypropylene, syndiotactic polypropylene, and propylene random, block or impact copolymers.

Typical ethylene based polymers have a density in the range of from 0.86 g/cc to 0.97 g/cc, a weight average molecular weight to number average molecular weight ($M_w/M_n$) of greater than 1.5 to about 10 as measured by gel permeation chromatography, a melt index ($I_2$) as measured by ASTM-D-1238-E in the range from 0.01 dg/min to 1000 dg/min, a melt index ratio ($I_{21}/I_2$) (I21 is measured by ASTM-D-1238-F) of from 10 to less than 25, alternatively a $I_{21}/I_2$ of from greater than 25, more preferably greater than 40.

Polymers produced by the polymerization process are useful in such forming operations as film, sheet, and fiber extrusion and co-extrusion as well as blow molding, injection molding and rotary molding; films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications; fibers include melt spinning, solution spinning and melt blown fiber operations for use in woven or non-woven form to make filters, diaper fabrics, medical garments, geotextiles, etc; extruded articles include medical tubing, wire and cable coatings, geomembranes, and pond liners; and molded articles include single and multi-layered constructions in the form of bottles, vessels, large hollow articles, rigid food containers and toys, etc.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

The foregoing description of the invention including but not limited to drawing and example are intended to illustrate one or more embodiments of the invention and are non-limiting. While the invention has been illustrated an described herein in terms of the advantages, features, and applications disclosed, it will be apparent to a person of ordinary skill in the art that the invention can be used in other instances. Other modifications and improvements can be made without departing from the scope of the invention.

We claim:

1. A process for quenching a reactor effluent stream from an oxygenate to olefins reactor, the process comprising the steps of:

(a) quenching the reactor effluent stream in a first quench stage with a first quench medium comprising an aqueous solution to form a first liquid fraction and a first effluent stream, wherein catalyst fines are washed from the reactor effluent stream into the first liquid fraction;

(b) quenching the first effluent stream in a second quench stage wit the first quench medium producing a second liquid fraction and a second effluent stream, wherein the second liquid fraction is cooled to form the first quench medium;

(c) settling catalyst fines entrained in the first liquid fraction in a first settling vessel;

(d) removing at least a portion of the first liquid fraction from the first settling vessel, wherein the first quench stage comprises a quench fitting and a first settling vessel, the first settling vessel having a top end, a bottom end, a first passage at the top end, a first outlet at the bottom end, and a second outlet between the top end and the bottom end;

(e) withdrawing the first effluent stream through the first passage;

(f) separating, in the first settling vessel, a first portion of catalyst fines in the first liquid fraction from a partially clarified first liquid fraction, the partially clarified first liquid fraction comprising a second portion of the catalyst fines;

(g) withdrawing first concentrated fines stream comprising the first portion or catalyst fines from the first outlet;

(h) withdrawing the partially clarified first liquid fraction from the second outlet, wherein the partially clarified liquid fraction is directed to a second settling vessel, the partially clarified liquid stream further comprises a hydrocarbon phase;

(i) withdrawing a second concentrated fines stream from the second sealing vessel, the second concentrated fines stream comprises substantially all of the second portion of catalyst fines from the second settling vessel;

(j) combining the second concentrated fines stream with the first concentrated fines stream;

(k) withdrawing a clarified aqueous stream; and (l) withdrawing a non-aqueous stream.

2. The process of claim 1, wherein the reactor effluent stream comprises olefin product and water, the reactor effluent stream further being entrained with the catalyst fines, wherein the first liquid fraction has no more than 20 wt. % water based upon the weight of water in the reactor effluent stream and a majority of catalyst fines based upon the amount of catalyst fines in the reactor effluent stream.

3. The process of claim 1, wherein the reactor effluent stream comprises olefin product and water, the reactor effluent stream further being entrained with the catalyst fines, wherein the second quench stage removes a majority of water based upon the amount of water in the reactor effluent stream.

4. The process of claim 1, wherein the reactor effluent stream comprises olefin product and methanol, the reactor effluent stream further being entrained with the catalyst fines, wherein a third quench stage removes a majority of methanol based upon the amount of water in the effluent stream.

5. The process of claim 1, wherein the reactor effluent stream comprises olefin product, methanol, and water, the reactor effluent stream further being entrained with the catalyst fines, wherein:

the first liquid fraction has no more than 20 wt. % water based upon the weight of water in the reactor effluent stream and a majority of catalyst fines based upon the amount of catalyst fines in the reactor effluent stream;

the second quench stage removes a majority of water based upon the amount of water in the reactor effluent stream; and a third quench stage removes a majority of methanol based upon the amount of methanol in the reactor effluent stream.

6. The process of claim 1, wherein the clarified aqueous stream comprises water and methanol, the process further comprising the steps of:

separating the clarified aqueous stream into a methanol fraction and a water fraction; and feeding the methanol fraction into the oxygenate to olefin reactor.

7. The process of claim 1, wherein the quench fitting is a tubular member comprising a plurality of spray nozzles configured to spray the first quench medium into the reactor effluent stream.

8. The process of claim 5, wherein the second quench stage has a first quench inlet and a second quench inlet located above the first quench inlet, the process further comprising the step of:

introducing the first quench medium into the first quench inlet at a first temperature and the second quench inlet at a second temperature that is at least about 2.7° C. lower than the first temperature.

9. The process of claim 8, wherein the second temperature is at least 5.6° C. lower than the first temperature.

10. The process of claim 8, wherein the second temperature is at least 11° C. lower than the first temperature.

11. The process of claim 8, wherein the second quench stage further comprises a first condensate outlet, the process further comprising the steps of:

withdrawing a portion of the second liquid fraction from the first condensate outlet; and directing the portion of the second liquid fraction to the first quench inlet and the second quench inlet.

12. The process of claim 1, wherein the third quench stage comprises a second condensate outlet, the process further comprising the step of withdrawing the third liquid fraction from the second condensate outlet and combining it with the clarified aqueous stream.

13. A process for quenching a reactor effluent stream from an oxygenate to olefins reactor, the process comprising the steps of:

(a) quenching the reactor effluent stream in a first quench stage with a first quench medium comprising an aqueous solution to form a first liquid fraction and a first effluent stream, wherein catalyst fines are washed from the reactor effluent stream into the first liquid fraction;

(b) quenching the first effluent stream in a second quench stage with the first quench medium producing a second liquid fraction and a second effluent stream, wherein the second liquid fraction is cooled to form the first quench medium;

(c) settling catalyst fines entrained in the first liquid fraction in a first settling vessel;

(d) removing at least a portion of the first liquid fraction to a second settling vessel and forming a clarified aqueous liquid; and (e) removing the clarified aqueous liquid from the second settling vessel.

14. The process of claim 13, wherein the clarified aqueous liquid removed from the second settling vessel is processed to remove methanol.

15. The process of claim 14, wherein the processing to remove methanol is by distillation.

16. The process of claim 13, wherein at least a portion of the first liquid stream in the first settling vessel is removed as a concentrated fines stream.

* * * * *